(12) United States Patent
Simpson et al.

(10) Patent No.: US 7,655,022 B2
(45) Date of Patent: Feb. 2, 2010

(54) COMPLIANT GUIDING CATHETER SHEATH SYSTEM

(75) Inventors: John A. Simpson, Carlsbad, CA (US); Wade Bowe, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 641 days.

(21) Appl. No.: 10/424,333

(22) Filed: Apr. 28, 2003

(65) Prior Publication Data

US 2004/0215228 A1 Oct. 28, 2004

(51) Int. Cl.
*A61B 18/24* (2006.01)
*A61M 29/00* (2006.01)
*A61N 1/05* (2006.01)

(52) U.S. Cl. .................. 606/194; 606/41; 606/108; 607/122

(58) Field of Classification Search ........... 604/96–102, 604/164, 171, 280, 96.01, 101.01, 103.02, 604/103.04, 103.06, 103.08; 600/3, 585, 600/264, 434, 435; 606/191, 192, 198, 158, 606/41, 194, 200; 607/122
See application file for complete search history.

(56) References Cited

U.S. PATENT DOCUMENTS

| | | | | |
|---|---|---|---|---|
| 4,771,777 A * | 9/1988 | Horzewski et al. | .......... | 606/194 |
| 5,179,961 A * | 1/1993 | Littleford et al. | ............ | 600/585 |
| 5,203,772 A * | 4/1993 | Hammerslag et al. | ....... | 604/528 |
| 5,254,107 A * | 10/1993 | Soltesz | ........................ | 604/525 |
| 5,295,959 A * | 3/1994 | Gurbel et al. | .......... | 604/103.13 |
| 5,308,356 A * | 5/1994 | Blackshear et al. | ......... | 606/194 |
| 5,324,269 A * | 6/1994 | Miraki | ........................ | 604/160 |
| 5,395,333 A * | 3/1995 | Brill | ........................ | 604/101.05 |
| 5,516,336 A * | 5/1996 | McInnes et al. | ............ | 606/194 |
| 5,545,132 A * | 8/1996 | Fagan et al. | ............ | 604/103.08 |
| 5,571,088 A * | 11/1996 | Lennox et al. | ........... | 604/96.01 |
| 5,571,161 A * | 11/1996 | Starksen | ..................... | 607/122 |
| 5,775,327 A | 7/1998 | Randolph et al. | | |
| 5,795,325 A * | 8/1998 | Valley et al. | ................. | 604/509 |
| 5,876,373 A * | 3/1999 | Giba et al. | ............... | 604/95.04 |
| 6,021,340 A * | 2/2000 | Randolph et al. | ........... | 600/381 |
| 6,036,697 A * | 3/2000 | DiCaprio | .................... | 606/108 |
| 6,122,552 A * | 9/2000 | Tockman et al. | ............ | 607/116 |
| 6,126,635 A | 10/2000 | Simpson et al. | | |
| 6,234,952 B1 * | 5/2001 | Liprie | ........................... | 600/3 |
| 6,267,747 B1 * | 7/2001 | Samson et al. | ........ | 604/103.07 |
| 6,287,319 B1 * | 9/2001 | Aboul-Hosn et al. | ........ | 606/192 |
| 6,290,697 B1 | 9/2001 | Tu et al. | | |
| 6,416,511 B1 | 7/2002 | Lesh et al. | | |
| 6,743,227 B2 * | 6/2004 | Seraj et al. | .................... | 606/41 |

* cited by examiner

*Primary Examiner*—Anhtuan T Nguyen
*Assistant Examiner*—Kathleen Sonnett
(74) *Attorney, Agent, or Firm*—Hollingsworth & Funk, LLC

(57) ABSTRACT

A guiding catheter system employs a compliant shaft with an inflatable balloon affixed to a distal portion of the shaft. The inflatable balloon includes channels that allow some amount of blood to flow past the balloon when inflated in a blood vessel. One or more inflation lumens is in fluid contact with the balloon and allows inflating the balloon from a proximal end of the catheter. A series of perfusion orifices may be included on the shaft proximal to the balloon.

8 Claims, 4 Drawing Sheets

COMPLIANT GUIDING CATHETER SHEATH SYSTEM

FIELD OF THE INVENTION

The invention relates generally to guiding catheter systems, and, more particularly, to guiding catheters for accessing the coronary sinus and other heart vessels.

BACKGROUND OF THE INVENTION

Guiding catheters are instruments that allow a physician to locate and cannulate vessels in a patient's heart for performing various medical procedures, including venography and implanting of cardiac pacing devices. Cannulating heart vessels requires navigating a small diameter, flexible guide through convoluted vasculature into a heart chamber, and then into a destination heart vessel. Once the destination heart vessel is reached, the catheter acts as a conduit for insertion of payloads into the vessel.

Once the vessel has been cannulated by a guiding catheter, an occlusion device may be utilized to hold the distal end of the guiding catheter in place during various procedures. The occlusion device blocks blood flow through the vessel at the same time lodging the catheter in place.

However, the blood flow cannot be blocked indefinitely, as occlusion of blood flow may cause detrimental effects on the patient. Therefore the clinician must be concerned about leaving the occluding device in place for too long. There is a need in the art for an improved guiding catheter for accessing heart vessels that can be guided through a convoluted pathway and lodged for a longer period of time in a blood vessel. The present disclosure discusses these and other needs in the art.

SUMMARY OF THE INVENTION

The present invention discloses a guiding catheter that can provide access to venous structures for medical procedures and be firmly lodged in those vessels while still allowing some amount of blood flow in the vessels.

In one embodiment, a guiding catheter for use with a guide apparatus for cannulating a blood vessel includes a flexible shaft having an open lumen. The open lumen is placeable over the guide apparatus so that the flexible shaft substantially assumes the shape of the guide apparatus. The guiding catheter includes a balloon at a distal portion of the flexible shaft. The balloon includes one or more external channels. An inflation lumen is disposed along the flexible shaft and in fluid connection with the balloon. Pressurization of a fluid in the inflation lumen inflates the balloon. The inflated balloon is arranged to lodge in the blood vessel and permit an external fluid flow through the external channels.

In one arrangement, the guiding catheter further includes one or more perfusion orifices of the flexible shaft proximal to the balloon. The perfusion orifices are in fluid connection with the external fluid flow and the open lumen of the flexible shaft. The balloon may be configured to include a plurality of expansion lumens, the external channels defined between adjacent expansion lumens. In some arrangements, the balloon may include three or four expansion lumens. The three expansion lumen arrangement may be configured to define an approximately triangular cross sectional shape.

The external channels of the balloon may be oriented substantially parallel to a centerline of the flexible shaft. In another arrangement, the external channels include a helical channel extending from a distal end of the balloon to a proximal end of the balloon.

In another embodiment of the present invention, a method of cannulating a destination vessel involves introducing a guide apparatus into the destination vessel. A guiding catheter is placed over the guide apparatus so that a distal portion of the guiding catheter is disposed in the destination vessel. A balloon disposed on a distal portion of the guiding catheter may be inflated so that the distal portion of the guiding catheter is lodged in the destination vessel and an external flow is permitted through an external channel of the balloon.

Introducing the guide apparatus in the destination vessel may involve actuating a steering mechanism of the guide apparatus to direct a distal end of the guide apparatus. In another arrangement, introducing the guide apparatus in the destination vessel involves manipulating a pre-shaped distal portion of the guide apparatus to direct a distal end of the guide apparatus.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
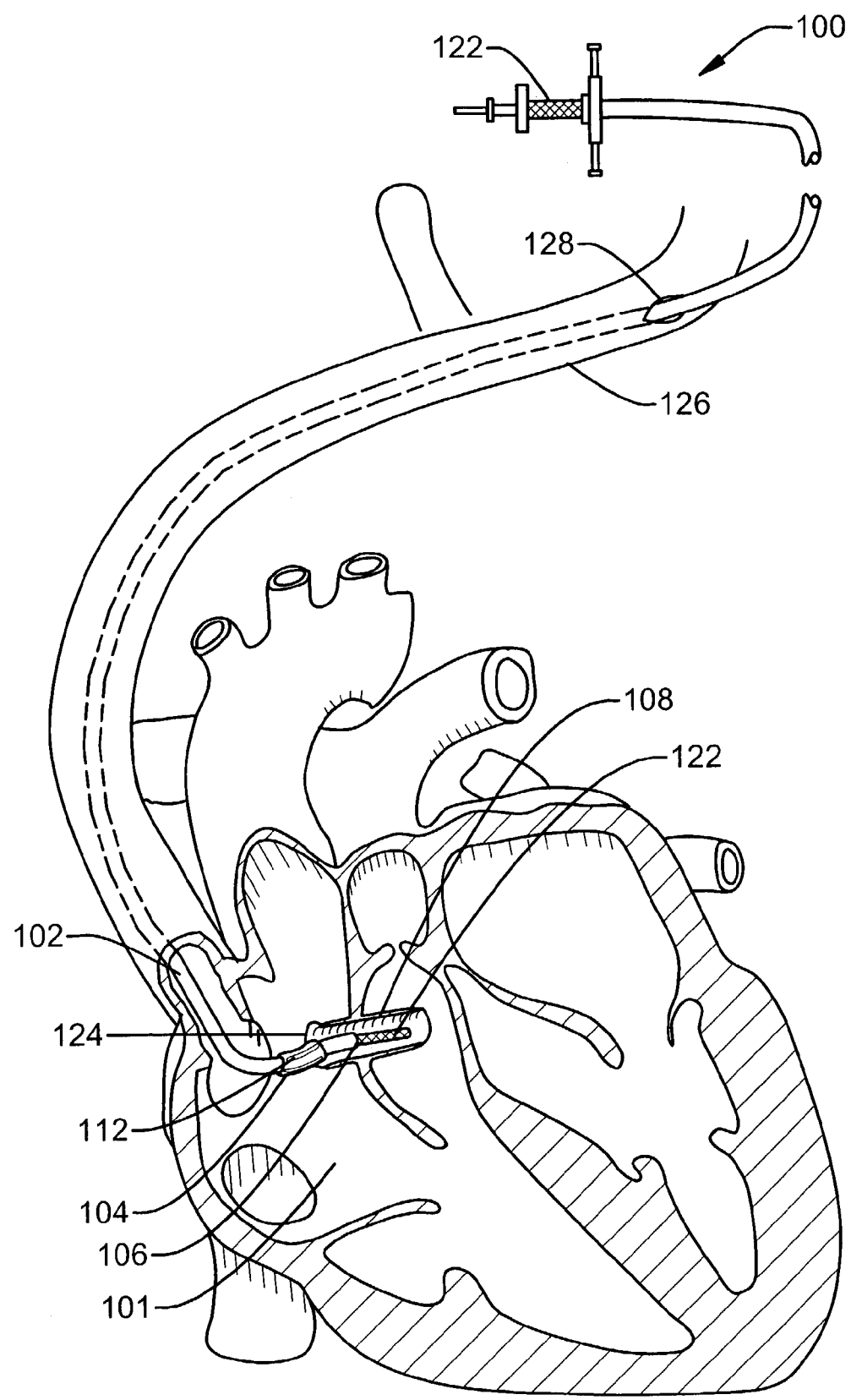
FIG. 1 is a cutaway view of a heart, showing a guiding catheter according to embodiments of the present invention deployed in the right atrium.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, a guiding catheter according to embodiments of the present invention employs a flexible shaft having a balloon attached at a distal end. The balloon has channels that allow fluid to flow past the inflated balloon. The guiding catheter includes an open lumen in the flexible shaft adapted for the introduction of payloads through the catheter system. The guiding catheter can be placed over a smaller maneuverable guiding apparatus that is used to locate a vessel. In one application, the guiding catheter can be used to introduce a payload into the coronary sinus or other heart vessels.

Turning now to FIG. 1, a guiding catheter, generally indicated by reference numeral 100, is shown deployed in the right atrium 101 of the heart. The guiding catheter 100 includes a flexible shaft 102 with an open lumen, and an inflatable balloon 104 at a distal end of the shaft 102. A distal tip 106 of the catheter 100 is positioned in the coronary sinus 108. The balloon 104 can be inflated to lodge the flexible shaft 102 in the coronary sinus 108.

The balloon 104 contains channels 112 that allow an external flow of blood to move past the lodged catheter shaft 102. In general, the term "external flow" as used herein generally refers to a flow past the outer surfaces of the catheter shaft 102 and the balloon 104. By providing a bypass external blood flow, the balloon 104 can advantageously remain inflated in place for longer periods of time. Once the balloon 104 is lodged into place, the flexible catheter shaft 102 can act as a guide for other devices such as contrast media, implantable leads, and diagnostic devices.

Implantation procedures may vary depending on the goal of the procedure and the condition of the patient. For purposes of example, one procedure for implanting a pacing lead into the coronary sinus 108 will be described in relation to FIG. 1. A maneuverable guide apparatus 122 may first be guided into the right atrium 101 to locate the ostium 124 of the coronary sinus 108. The guide apparatus 122 may be any type of pre-shaped and/or steerable apparatus. For purposes of illustration, the guide apparatus 122 will be described as a pre-shaped, steerable electrophysiology (EP) catheter.

During the EP catheterization procedure, a clinician inserts the EP catheter 122 into an access vessel 126 through an incision or introducer sheath puncture 128. The access vessel 126 may include any of the large veins of the upper limb system such as the cephalic or subclavian veins. Lower limb vessels such as the femoral artery are also used as access points for many heart cannulation procedures.

Once the EP catheter 122 is in the right atrium, the shape and/or steering apparatus of the EP catheter 122 may be used to assist in locating the coronary sinus ostium 124. The EP catheter 122 may also contain distal electrodes (not shown) that assist in locating the ostium 124. Signals from the electrodes can be used to "map" electrical activity of the heart tissues. Once the clinician has found the coronary sinus ostium 124, the guiding catheter 100 may be slid over the EP catheter 122 to introduce the guiding catheter 100 into the coronary sinus 108.

In an alternate approach to placing the guiding catheter 100 in the coronary sinus 108, the guiding catheter 100 may be first introduced into the access vessel 126 and into the right atrium 101. After the distal tip 106 of the guiding catheter 100 is located in the right atrium 101, the EP catheter 122 can be placed into the open lumen of the guiding catheter 100 so that the EP catheter 122 emerges into the right atrium 101. The guiding features of the EP catheter 122 can then be used to locate the coronary sinus ostium 124, after which the guiding catheter 100 can be slid over the EP catheter 122 into the coronary sinus 108.

The flexible shaft 102 of the guiding catheter 100 is typically made relatively compliant so that the shaft 102 can be placed over a guide apparatus without substantially disturbing the shape of the apparatus. This compliant shaft 102 also helps reduce anatomical trauma during placement procedures. Once the guiding catheter 100 is fully seated in position, the balloon 104 can be inflated to hold the flexible shaft 102 in place. The inflated balloon 104 provides the catheter 100 with an anchor point to prevent dislodgment of the shaft 102 during further procedures.

Once the guiding catheter 100 is lodged into place, the EP catheter 122 can be removed. The guiding catheter 100 remains as a conduit for payloads directed to the heart. In one example, a contrast media can be injected into the flexible shaft 102 for fluoroscopic mapping of coronary vessels. It is appreciated that the channels 112 of the inflated balloon 104 may allow some small amount of the contrast media to flow out of the coronary sinus 108. However, the contrast media has significantly greater viscosity than blood, therefore this "backflow" of contrast media will be minimized.

After performing fluoroscopy, a device such as a pacing lead may be implanted into a branch vessel of the coronary sinus 108. In one procedure, the pacing lead is inserted into the guiding catheter 100 until in emerges into the coronary sinus 108. A stylet or guidewire may be used to assist placing the pacing lead in the branch vessel. A finishing wire or other fixing device can be inserted to hold the pacing lead into place, after which the balloon 104 can be deflated and the flexible shaft 102 of the catheter 100 withdrawn. The shaft 102 may include peel away features such as a longitudinal pre-stress on the shaft walls that allow the shaft 102 to be peeled apart as it is withdrawn. Finally, after withdrawing the shaft 102, the finishing wire or fixing device is removed to complete the procedure.

Figure 2:
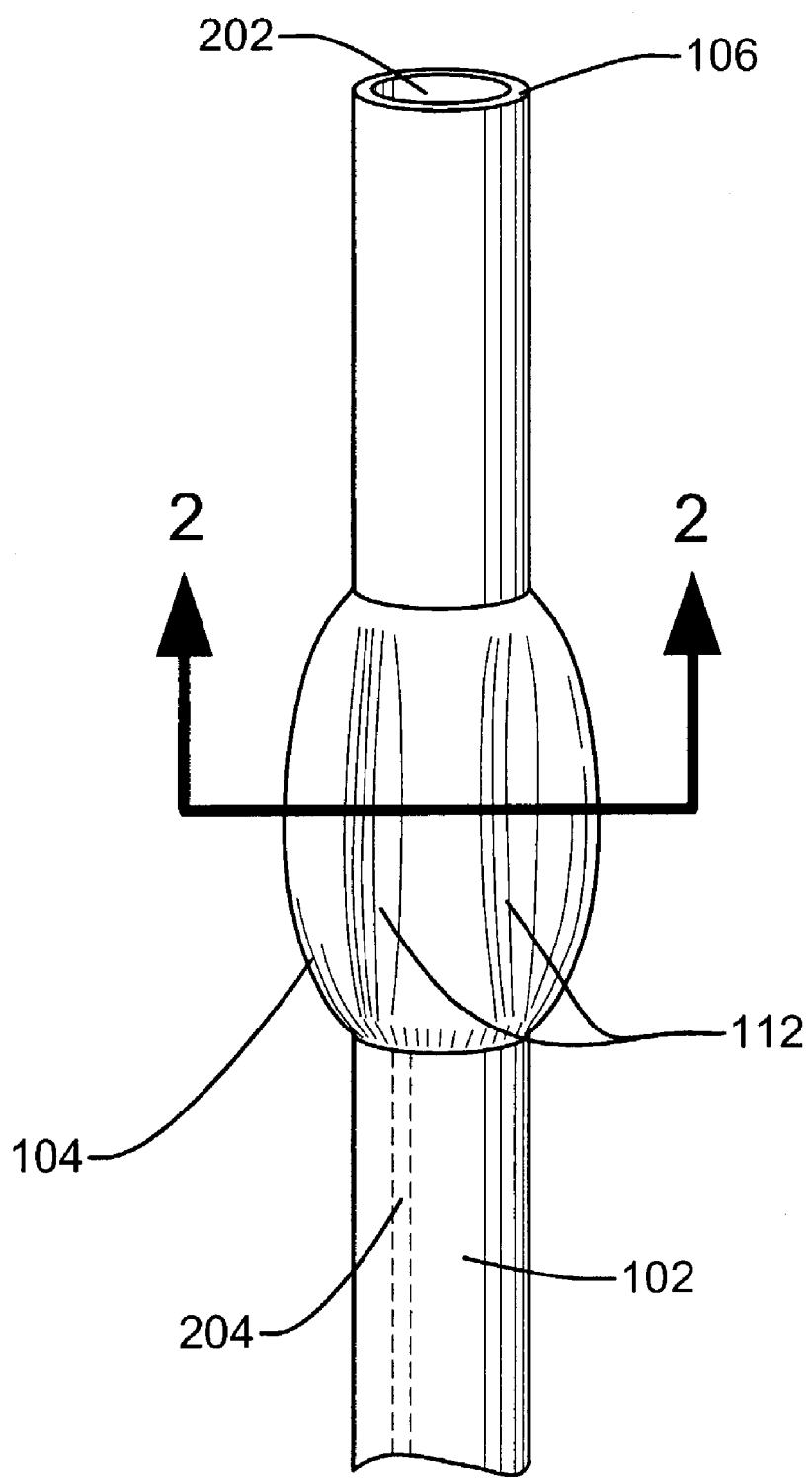
FIG. 2 is a side view of a distal end of the catheter according to embodiments of the present invention.

Turning now to FIG. 2, construction details of the guiding catheter 100 are illustrated. The shaft 102 is typically an elongated tubular member having an open guide lumen 202. The guide lumen 202 is formed to allow the shaft 102 to be introduced over guide apparatus as well as acting as a conduit for payloads introduced into the catheter 100.

The balloon 104 is fixably mounted at a distal portion of the shaft 102. The balloon 104 is in fluid contact with one or more inflation lumens 204 used to inflate and deflate the balloon 104. The inflation lumens 204 may be formed on an inside or outside surface of the flexible shaft, or the inflation lumens 204 may be formed within the walls of the flexible shaft 102. The inflation lumens 204 are accessible from the proximal end of the catheter 100, thereby allowing the clinician to inflate and deflate the balloon 104 using a proximal device such as a syringe.

The balloon 104 contains channels 112 that allow blood flow to bypass the inflated balloon 104. In FIG. 2, these channels 112 are oriented approximately parallel to the centerline of the shaft 102. This orientation of the channels 112 is typical, since it also corresponds to the direction of blood flow in the blood vessel. However, other orientations of the channels 112 may be used, assuming the channels 112 allow blood to flow past the inflated balloon 104.

Figures 3, 4:
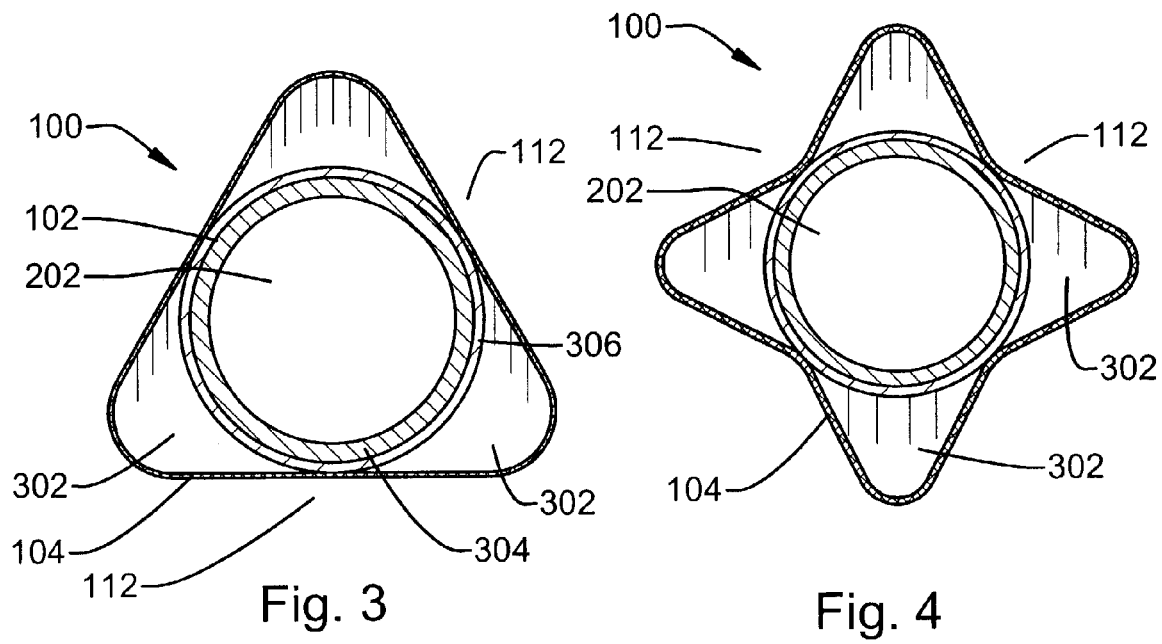
FIG. 3 is a cross sectional view of the catheter and balloon of FIG. 2, corresponding to section 2-2 of FIG. 2.
FIG. 4 is a cross sectional view of the catheter shaft corresponding to section 2-2 of FIG. 2 showing an alternate cross sectional shape of the balloon.

The balloon 104 may be fabricated with any suitable cross sectional shape. Two exemplary cross sectional shapes are shown in FIGS. 3 and 4. In FIG. 3, the balloon 104 includes a substantially triangular cross sectional shape. The balloon 104 includes three expansion lumens 302 that expand to lodge against the walls of a blood vessel. The channels 112 are defined by the spaces between the expansion lumens 302. The balloon 104 may be bonded or otherwise affixed to the shaft 102 at portions of the balloon 104 that define the channels 112. The expansion lumens 302 may be in fluid connection with each other and the inflation lumens so that all expansion lumens 302 inflate simultaneously. Alternatively, each lumen 302 may have an associated inflation lumen so that each expansion lumen 302 is independently inflatable.

The flexible shaft 102 as illustrated in FIG. 3 may include an inner liner 304 and an outer sheath 306. The inner liner 304 may be formed of a lubricious material such as polytetrafluoroethylene (PTFE). The outer sheath 306 may be fabricated of a smooth, wear resistant polymer material. The distal tip 106 of the shaft (see FIG. 2) may include a soft covering to prevent tissue trauma when introducing the catheter 100 into blood vessels. The flexible shaft 102 may include other features such as a stainless steel braiding (not shown) embedded within the shaft walls to improve lateral and torsional stiffness.

In some configurations, the flexible shaft 102 is made without significant stiffening features such as a braid. A relatively compliant flexible shaft 102 can be made to more easily slide over an EP catheter or other guide apparatus. A compliant shaft 102 is less likely to "overpower" the shape of a guide apparatus in such a situation and is less likely to induce tissue trauma along the guide path. Finally, a compliant shaft 102 is more easily withdrawn and easier to peel away should a pre-stress feature be included in the shaft walls.

Because the catheter 100 can be introduced over a guide apparatus, the flexible shaft 102 can be made without any pre-shaped curve or variable flexibility along the shaft's length. This allows the catheter 100 to be fabricated for general-purpose use. In general, the catheter 100 can be used with any guide apparatus that will fit within the guide lumen 202 of the catheter 100.

Turning now to FIG. 4, a four-lobed balloon 104 is illustrated. As with the triangular shape of FIG. 3, the portions of the balloons defining the channels 112 may be bonded or otherwise fixed to the shaft 102. The four expansion lumens 302 may be in fluid connection with each other or independently inflatable.

Figure 5:
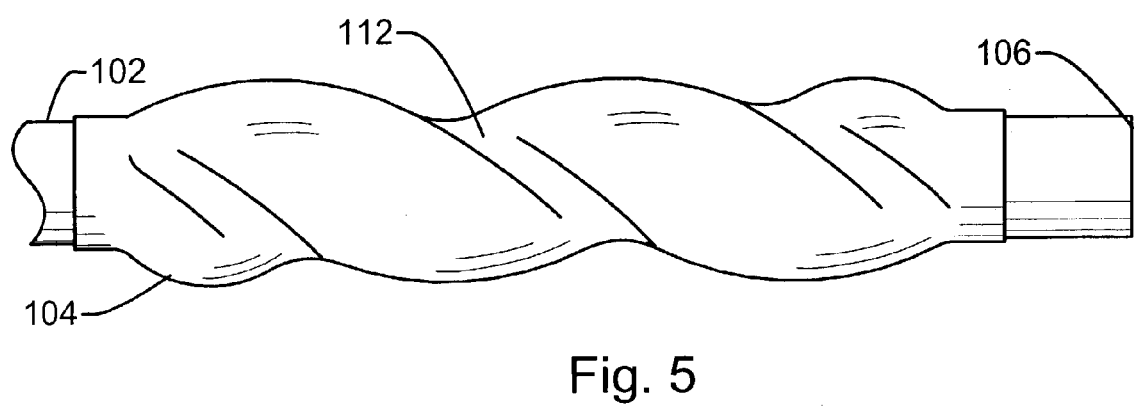
FIG. 5 is a side view of a distal end of a catheter illustrating a helical channel arrangement according to embodiments of the present invention.

Although the channels 112 may be oriented substantially parallel to the centerline of the flexible shaft 102, other channel orientations may be possible. For example, FIG. 5 shows a helical channel 112 extending along the balloon 104. Such a helical channel 112 may provide the balloon 104 with a more secure contact surface when the balloon 104 is inflated in a blood vessel.

Figure 6:
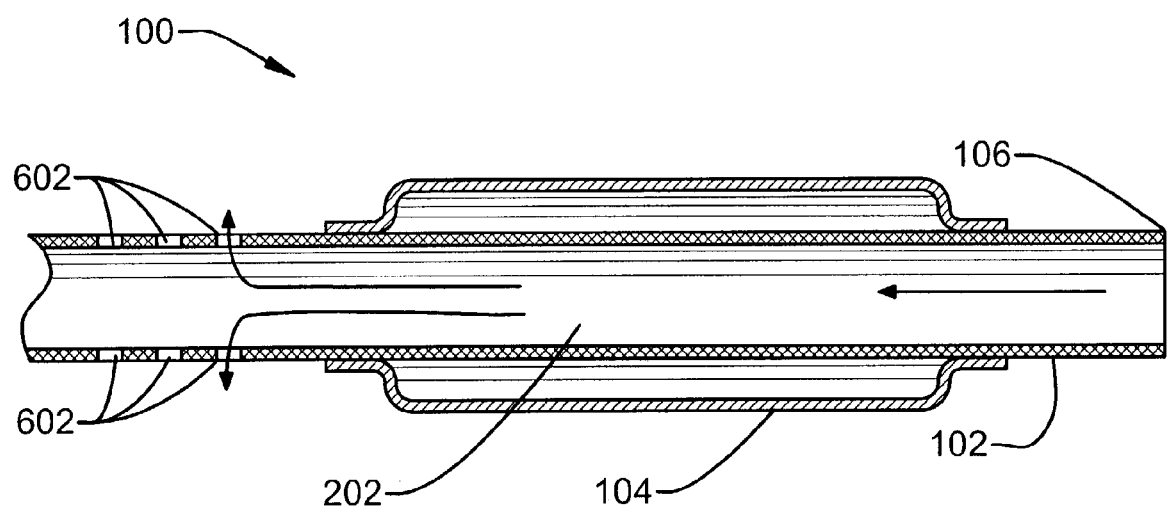
FIG. 6 is a cross sectional view of the catheter showing perfusion orifices according to embodiments of the present invention.

Additional features may be included with a catheter 100 according to embodiments of the present invention to increase the amount of bypass blood flow. For example, FIG. 6 shows a cross sectional view of a distal portion of the catheter's flexible shaft 102. A series of perfusion orifices 602 are included on a portion of the shaft walls proximate the balloon 104. The perfusion orifices 602 are in fluid connection with the guide lumen 202 and an external flow outside the flexible shaft 102.

Blood can enter the guide lumen 202 through the distal tip 106 of the flexible shaft 102 and can exit through the orifices 602 as indicated by the bold arrows. Blood can also flow in a direction opposite that indicated by the arrows. The effectiveness of the perfusion orifices 602 may depend on the size of any payload deployed within the catheter 100, as large payloads may block the guide lumen 202 to some extent. It is appreciated that the combination of bypass features of the balloon 104 and the perfusion orifices 602 may provide enhanced bypass blood flow in many applications.

From the description provided herein, those skilled in the art are readily able to construct and use a guiding catheter according to embodiments of the present invention. It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of cannulating a coronary blood vessel branching from a coronary sinus of a patient's heart, comprising:

locating a coronary sinus using a guide apparatus having a distal end with a pre-formed curve;

introducing the guide apparatus into the coronary sinus;

sliding an open lumen of a guiding catheter over the distal end of the guide apparatus so that a distal portion of the guiding catheter is advanced through the coronary sinus and into the coronary blood vessel, the guiding catheter comprising a flexible shaft that substantially assumes the shape of the guide apparatus without disturbing the shape of the distal end of the guide apparatus when the open lumen of the guiding catheter is slid over the guide apparatus, the open lumen of the guiding catheter dimensioned to receive an implantable pacing lead, a distal portion of the flexible shaft devoid of a pre-shaped curve and comprising a balloon;

inflating the balloon so that the distal portion of the guiding catheter is anchored within the coronary sinus by engagement of the balloon with the vessel walls of the coronary sinus to lodge the balloon within the coronary sinus at an anchor point, the inflated balloon comprising one or more external channels continuous from a distal end of the balloon to a proximal end of the balloon that facilitate flow of blood past the inflated balloon and through the coronary sinus while the balloon is inflated in the coronary sinus;

removing the guide apparatus from the guide lumen of the guiding catheter while the guiding catheter is held in place by the inflated balloon at the anchor point;

advancing an implantable pacing lead through the open lumen of the guiding catheter for placement within the coronary blood vessel while the guiding catheter is held in place by the inflated balloon at the anchor point;

deflating the balloon after the implantable pacing lead has been placed in the coronary blood vessel; and removing the guiding catheter and leaving the implantable pacing lead in the coronary blood vessel.

2. The method of claim 1, wherein locating the coronary sinus using the guide apparatus comprises actuating a steering mechanism of the guide apparatus to direct the distal end of the guide apparatus.

3. The method of claim 1, wherein the maneuverable guide apparatus is the first component used in the method to be guided into the coronary sinus.

4. The method of claim 1, further comprising peeling the flexible shaft along one or more longitudinal pre-stressed features after the implantable pacing lead has been placed in the coronary blood vessel, wherein inflating the balloon further comprises pressurizing an inflation lumen disposed on an exterior surface of the flexible shaft, the inflation lumen in fluid communication with the balloon.

5. The method of claim 1, further comprising mapping the electrical activity of the heart using an electrode on the distal end of the guide apparatus, the electrical map facilitating location of the coronary sinus using the guide apparatus.

6. The method of claim 1, further comprising injecting contrast media into the coronary sinus through the guiding catheter when the balloon has been inflated and after the guiding apparatus has been removed such that some amount of the injected contrast media flows past the inflated balloon through the one or more external channels and out of the coronary sinus into the right atrium.

7. The method of claim 1, wherein the guiding catheter comprises an outside surface and the balloon is bonded to the outside surface along the length of each of the one or more external channels.

8. The method of claim 1, wherein the balloon is a multi-lobed balloon comprising at least three external channels.

* * * * *

UNITED STATES PATENT AND TRADEMARK OFFICE
CERTIFICATE OF CORRECTION

PATENT NO.      : 7,655,022 B2                                              Page 1 of 1
APPLICATION NO. : 10/424333
DATED           : February 2, 2010
INVENTOR(S)     : Simpson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1150 days.

Signed and Sealed this

Twenty-third Day of November, 2010

David J. Kappos
*Director of the United States Patent and Trademark Office*